United States Patent [19]

Powell

[11] Patent Number: 5,086,756
[45] Date of Patent: Feb. 11, 1992

[54] HAND OPERATED ORAL IRRIGATION DEVICE FOR PACKAGED LIQUIDS

[76] Inventor: James R. Powell, 480 Roe Ave., Elmira, N.Y. 14901

[21] Appl. No.: 637,142

[22] Filed: Jan. 3, 1991

[51] Int. Cl.⁵ .............................................. A61H 7/00
[52] U.S. Cl. ..................................... 128/66; 222/498
[58] Field of Search ............... 128/66; 433/80; 222/74, 222/79, 498, 499, 540

[56] References Cited

U.S. PATENT DOCUMENTS

| | | | |
|---|---|---|---|
| Re. 32,354 | 2/1987 | Savage | 222/499 |
| 3,050,218 | 8/1962 | Harvey | 222/498 |
| 3,144,867 | 8/1964 | Trupp et al. | 128/66 |
| 3,318,482 | 5/1967 | Voce | 222/79 |
| 3,480,009 | 11/1969 | Sinai | 128/66 |
| 4,592,728 | 6/1986 | Davis | 433/80 |
| 4,803,974 | 2/1989 | Powell | 128/66 |

*Primary Examiner*—John J. Wilson
*Attorney, Agent, or Firm*—Fleit, Jacobson, Cohn, Price, Holman & Stern

[57] ABSTRACT

A device for irrigating the oral cavity with liquid from a commercially available, factory prepared package or container which includes a discharge nozzle and a hand operated pump unit for delivering an antiplaque or similar liquid of therapeutic value to areas in the oral cavity which are remote and difficult to reach. The package or container is provided with a female module having a specifically configured opening to accept a male module on the pump unit with the modules including interlocking components which are engaged and disengaged by a partial rotation and including a seal which provides a leak proof communication between the interior of the container or package and the pump unit with the configuration of the modules being such that a specific mating configuration must be used in order to connect the modules. The package or container includes an upper end portion that is openable and separate from the liquid containing portion to provide a storage area for the pump unit.

11 Claims, 2 Drawing Sheets

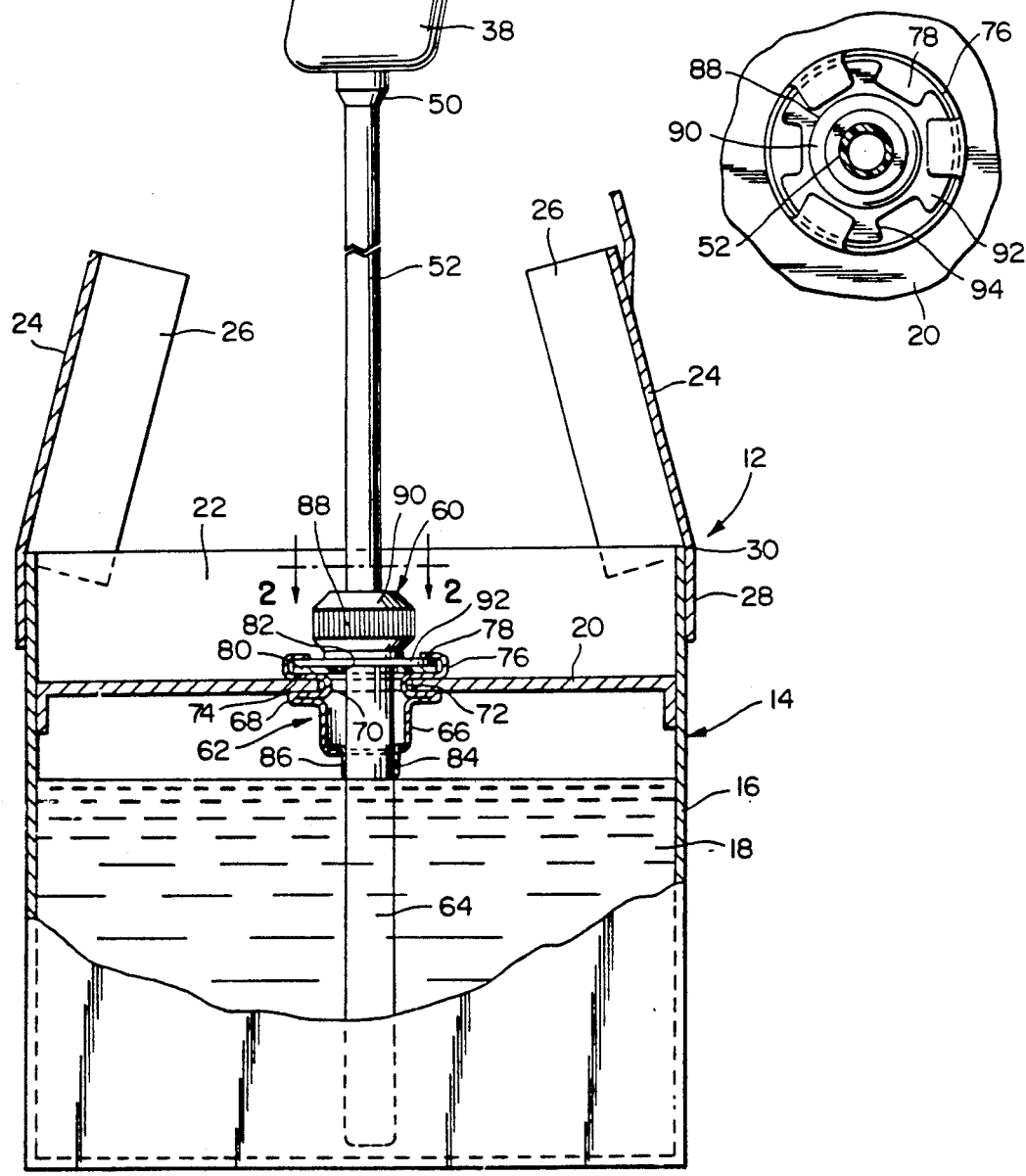

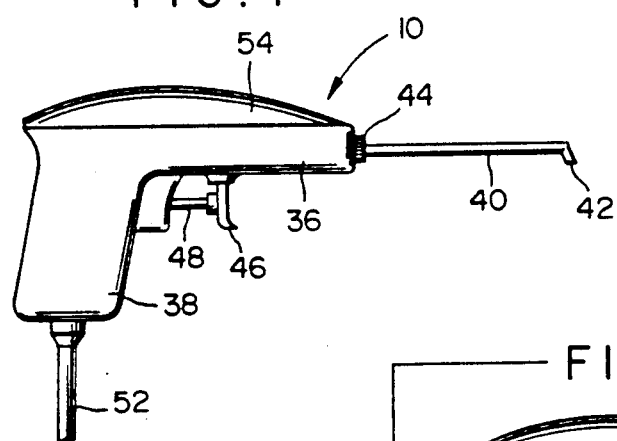
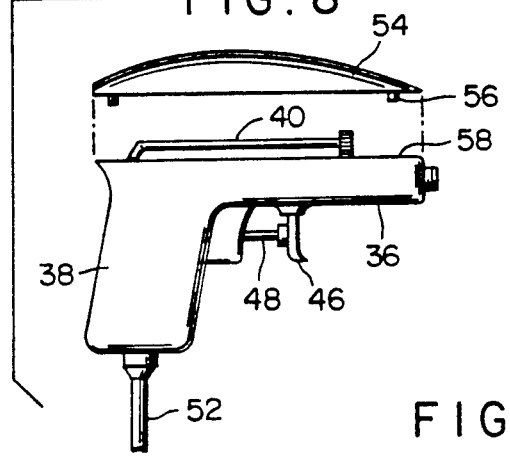
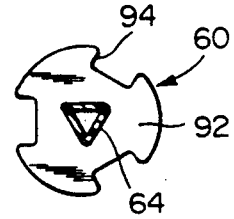
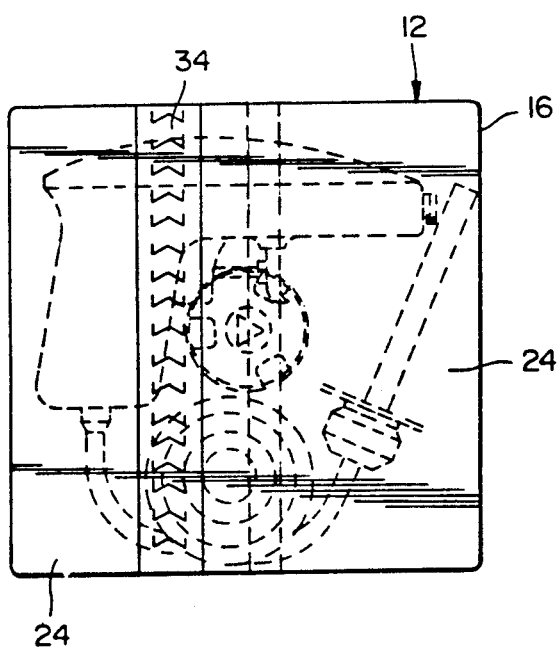
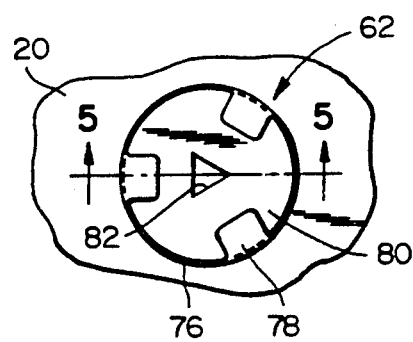
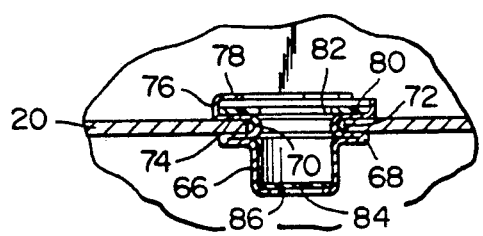

HAND OPERATED ORAL IRRIGATION DEVICE FOR PACKAGED LIQUIDS

BACKGROUND OF THE INVENTION

1. Field of the Invention

The present invention generally relates to a device for irrigating the oral cavity with liquid from a commercially available, factory prepared package or container which includes a discharge nozzle and a hand operated pump structure for delivering an antiplaque or similar liquid of therapeutic value to areas in the oral cavity which are remote and difficult to reach. The package or container is provided with a module or adaptor having a specifically configured opening to accept a module or adaptor on the pump unit with the modules or adaptors including interlocking components which are engaged and disengaged by a partial rotation and including a seal which provides a leak proof communication between the interior of the container or package and the pump unit with the configuration of the modules or adaptors being such that the specific mating configuration must be used in order to connect the modules or adaptors. The package or container includes an upper end portion that is openable and separate from the liquid containing portion to provide a storage area for the pump unit.

2. Description of the Prior Art

My prior U.S. Pat. No. 4,803,974 issued Feb. 14, 1989 for Oral Lavage Apparatus discloses a hand operated pump device connected with a liquid container and includes a discharge nozzle for irrigating an oral cavity. In this patent the container for the liquid is constructed to enable liquid from a bulk container or the like to be poured into the container to which the pump unit is connected by a flexible tube. This procedure exposes the liquid to ambient environmental conditions thus introducing the risk of contamination. The above-mentioned patent and the prior patents made of record in that patent do not disclose an arrangement in which the treating liquid is prepackaged with the pump unit and package or container for the liquid including interconnected modules and a seal structure enabling the treating liquid to be discharged directly and without contact with ambient air from the package through a connecting module o adaptor assembly to the hand operated pump unit for discharge into the oral cavity.

SUMMARY OF THE INVENTION

An object of the present invention is to provide a hand operated oral irrigation device for packaged liquids which includes a hand operated pump unit having a discharge nozzle capable of reaching into and being directed toward remote and generally inaccessible areas of the oral cavity to enable a therapeutic liquid to be discharged throughout the oral cavity with the pump unit being connected to the packaged liquid by interconnecting, separable modules including a seal assembly to provide a sealed, separable interconnection between the package and pump unit to eliminate air contact with the liquid being discharged from the package into the oral cavity.

Another object of the invention is to provide an oral irrigation device as set forth in the preceding object in which the packaged liquid is provided in a container having a separate compartment forming a storage area for the pump unit when not in use with the storage area including an openable closure to provide access to the pump unit while maintaining the aseptic characteristics of the liquid in the package.

A further object of the invention is to provide an oral irrigation device in accordance with the preceding objects in which the package or container is provided with a female module and the pump unit is provided with a male module having an interconnecting structure which requires partial relative rotation between the female and male modules to connect and disconnect the modules thereby providing a positive but secure mechanical interconnection between the modules for communicating the interior of the liquid package or container with the pump unit.

Still another object of the invention is to provide an oral irrigation device as set forth in the preceding objects in which the external surfaces of the interlocking components of the modules provide an effective seal between the interlocking components when they are locked in connected relation with the modules including specific unique configurations which require that modules of the same shape be used in order for them to be interconnected thereby permitting the use of only a specific product with the pump unit.

These together with other objects and advantages which will become subsequently apparent reside in the details of construction and operation as more fully hereinafter described and claimed, reference being had to the accompanying drawings forming a part hereof, wherein like numerals refer to like parts through-out.

BRIEF DESCRIPTION OF THE DRAWINGS

FIG. 1 is a side elevational view of the present invention illustrating the components in connected relation and ready for use.

FIG. 2 is a detailed sectional view taken substantially upon a plane passing along section line 2—2 on FIG. 1 illustrating further structural details of the interconnected modules or adaptors.

FIG. 3 is a bottom plan view of the male modular adaptor.

FIG. 4 is a top plan view of the female modular adaptor.

FIG. 5 is a transverse, sectional view taken along section line 5—5 on FIG. 4 illustrating further structural details of the female module or adaptor.

FIG. 6 is a top plan view of the liquid package illustrating the storage of the hand pump unit therein.

FIG. 7 is an elevational view of the hand operated pump unit forming a part of the present invention.

FIG. 8 is an elevational view thereof illustrating the openable top of the pump unit providing a storage area for a selectively used discharge nozzle.

DESCRIPTION OF THE PREFERRED EMBODIMENT

Referring now specifically now to the drawings, the oral irrigation device of this invention includes a hand operated pump unit generally designated by reference numeral 10 and a liquid package generally designated by numeral 12. The package 12 includes a container 14 defined by a peripheral wall 16 enclosing and containing a quantity of liquid 18 which has therapeutic values when used in the oral cavity such as a liquid which prevents, retards or removes plaque from the various surfaces of the teeth. The package 12 can be of any desired configuration and size in order to provide an adequate supply of liquid 18. As illustrated, the package 12 may be square or rectangular but it can be of other shape and configurations. The container 14 includes a top wall 20 which is spaced downwardly from the upper end of the peripheral wall 16 to provide a storage compartment 22 for the pump unit 10. The open top of the storage compartment 22 is provided with a pair of closure panels 24 which have downturned side flaps 26 which overlap the upper end portion of opposed portions of the peripheral wall. The outer edge of each of the panels 24 includes an attachment flap 28 secured to opposed portions of the peripheral wall 16 with a hinge axis 30 forming a juncture between the flaps 28 and panels 24 to enable the panels 24 to pivot between an open position as illustrated in FIG. 1 and a closed position illustrated in FIG. 6. The free edges of the panels 24 are interconnected by a closure strip 32 which includes a weakened tear off strip 34 to maintain the closure panels 24 in closed condition until access is desired to the pump unit 10. When the package 12 is closed, the pump unit 10 is sealed within the storage compartment 22 as illustrated in FIG. 3 with the tear strip 34 being removable to enable the closure panels to be opened to gain access to the pump unit and to also gain access to the top wall 20 of the container 14.

The pump unit 10 includes a housing 36 having a depending handle 38 at one end thereof which generally is in the configuration of a handgrip with the overall configuration of the pump unit being that of a handgun. A discharge tube 40 with a nozzle 42 at the outer end thereof is attached to the housing by a screw threaded or frictional connection 44. The underside of the housing 36 includes a hand operated trigger 46 and an operating rod 48 to operate the pump unit. The details of the pump structure are disclosed in prior U.S. Pat. No. 4,803,974. The handle 38 includes an adaptor 50 having a depending tube 52 connected thereto forming an inlet for the pump unit 10. The housing 36 includes a top removable or pivotal section 54 with the removable section 54 being hollow and provided with depending friction connectors 56 to engage with the inner peripheral edge of the top surface 58 on the housing 36 to enable storage of the tube 40 and nozzle 42 under the removable top portion 54 when the top portion is in closed position with the friction fasteners 56 engaging an inwardly facing edge of the top edge of the housing 36. Various types of connections such as pivotal connections may be provided for the top portion 54 to enable it to move between an open and closed position. The tube and nozzle may be connected to the housing by bellows type flexible tube section to enable the nozzle and straight portion of the tube to be bent back over top of the housing 36 and placed under the top portion 54 which would have an opening at the front to receive the connecting portion of the discharge tube.

The tube 52 which is flexible includes a male module generally designated by reference numeral 60 thereon for interlocking and sealed relation to a female module 62 incorporated in to the central portion of the top wall 20 with the lower end of the tube 64 having a length sufficient to reach to the lower end of the container 14 in order to remove substantially all of the liquid 18 therefrom with the bottom end of the tube 64 being spaced slightly above the bottom of the container 14 as illustrated in FIG. 1.

The female module 62 includes a generally cylindrical peripheral wall 66 depending from the top wall 20 as illustrated in FIG. 5 with the peripheral wall including an outwardly extending reversely bent flange 68 at the upper end thereof which forms the lower side of an outwardly facing U-shaped groove 70 receiving the peripheral edge of opening 72 in the top wall 20. The top flange of the U-shaped groove 70 is defined by a flange 74 which engages the upper surface of the top wall 20 outwardly of the opening 72. The outer edge of the flange 74 includes a short upturned wall 76 with the top edge of the wall 76 including three inwardly extending tabs 78 which are spaced equidistant around the periphery of the flange 76 as illustrated in FIG. 4. Positioned between the upper surface of the flange 74 and the tabs 78 is circular disk 80 having an opening 82 extending therethrough with the opening 82 being of triangular configuration as illustrated in FIG. 4. A puncturable seal 84 is connected to an interned flange 86 on the lower end of the cylindrical wall 66. The disk or washer 80 having the triangular opening 82 therein is rotatable in relation to the remainder of the module 62 which is crimped and sealed to the opening 72 in the top wall 20. The components of the module may be constructed of plastic or other similar material and forms a closure for the opening 72 to maintain the liquid 18 out of contact with ambient air. A removable dust cover may be placed over the upper surface of the module 62 when the package is sealed if desired.

The male component 60 on the tube 52 includes a generally cylindrical knob 88 rigid and integral with the tube 52 with the external surface thereof being serrated or knurled to facilitate gripping and rotation of the knob. The upper and lower surfaces of the knob may be tapered inwardly at 90. The lower end of the knob 90 is provided with a peripheral flange or disk 92 which has a plurality of equally spaced notches 94 therein which have a radial and peripheral extent sufficient to receive the tabs 78 therethrough. This enables the module 60 to be moved toward the module 62 and the flange 92 inserted past the tabs 68 which are aligned with and pass through the notches 94. The knob 88 along with the flange or disk 92 then can be rotated until the notches 94 are misaligned with the tabs 78 and a portion of the flange or disk 92 underlies and engages the tabs 78 thus locking the male module 60 to the female module 62. The depending tube 64 is substantially rigid but still somewhat flexible to enable it to penetrate the seal 84 when it is inserted through the female module 62.

The transverse configuration of the tube 64 is also triangular as illustrated in FIG. 3 which enables it to pass through the triangular opening 82 in the disk 80. This unique configuration of the opening 82 and the tube 64 assures that the proper product will be used with the pumping unit since a package having a different product would have a differently shaped opening in the disk. This shape relationship eliminates the possibility of a liquid other than one formulated for use in the oral cavity from being used with the pumping unit.

The modules 60 and 62 may be constructed of plastic material, metal or the like and the female module formed and crimped onto the top wall in sealed relation to the opening 72. The container may be constructed of plastic, cardboard with a liquid proof coating or lining or any other suitable material. If the top wall in constructed of plastic, the female module may be integral with and of unitary construction with the top wall. The specific shaped opening permits liquid flow and accepts the male module which is of similar shape. The relationship between the tabs 78, flange 92 and notches 94 is such that only about ¼ rotation of the male module is required thus enabling locking and unlocking of the male module in a quick and efficient manner. The external surfaces of the disks and the associated surfaces of the flanges of the male module and female module are constructed of material that will provide a seal when the parts are locked with the undersurfaces of the tabs 76 being slightly inclined to cam the flange 92 slightly toward the disk 80. The triangular configuration of the tube 64 and the opening 82 assures that only a specific product will be used with the pumping unit. The storage compartment for the pump unit may be integral with the package as shown or it could be a separate storage compartment so that it could be moved from one container to another and the pump unit may vary in configuration as may the specific construction of the tube and nozzle and the manner in which it is connected to the housing 36.

The package adapts itself for over-the-counter sales and also contemplates the use of a reusable case to receive a bag-type liner forming a refill for the case with the bag-type liner having the female module incorporated in the top surface thereof thus enabling the case to be reused and refilled bags placed in the case. The case could be closed with a pivotal or removable lid with the case forming a storage area for the pump unit when not in use since the case would be vacant after the refill bag has been emptied. The shape and configuration of the pumping unit may vary and may be a conventional type of pump/spray unit that is commercially available with the male module connected thereto in a manner to connect with the female module.

The oral irrigation device provides a delivery system for delivering a liquid in a pre-packaged container to the oral cavity in the form of a spray or stream under sufficient light pressure to enable the liquid to be deposited throughout the surface areas of the teeth and gums and other areas of the oral cavity. The liquid is discharged into the oral cavity without transfer of the liquid by pouring or other means which expose it to the outside air. The connecting modules enable the liquid to be propelled directly from the package through the connecting modules and through the pump unit for discharge.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. An oral irrigation device comprising the combination of a packaged liquid and a pump unit, said packaged liquid including a container having a quantity of liquid therein formulated to treat surfaces within an oral cavity, said container including a top wall having a female connecting module therein, said pump unit including discharge nozzle means to discharge liquid onto surfaces of the oral cavity, an inlet tube communicated with the pump unit, said inlet tube including a male connecting module for separable, sealing connection with the female connecting module on the container to communicate the inlet tube with the interior of the container thereby enabling discharge of the liquid directly from the container onto the surfaces of the oral cavity without coming onto contact with ambient air, said female connecting module including a tubular housing having an opening extending therethrough, said tubular housing extending through the top wall of the container and including a rotatable disk mounted therein, said disk including an opening therethrough having a non-circular configuration, said male connecting module including a tubular inlet member extending below the male connecting module and forming a continuation of the inlet tube with the inlet member including a transverse configuration identical to the opening in the disk to enable insertion of the tubular member but excluding insertion of tubular members of different shape.

2. The oral irrigation device as defined in claim 1 wherein the opening in the disk and the tubular member are triangular in cross-sectional configuration.

3. The oral irrigation device as defined in claim 1 wherein said housing includes a plurality of circumferentially spaced inwardly extending tabs at the upper end thereof, said male connecting module including a flange having a plurality of circumferentially spaced notches in the periphery thereof, said flange on the male connecting module passing into the housing when the notches are aligned with the tabs with the flange engaging the disk when inwardly of the tabs thereby enabling the flange to be rotated a partial turn to misalign the notches with respect to the tabs thereby locking the flange and male connecting module to the female connecting module.

4. The oral irrigation device as defined in claim 3 wherein the lower end of said housing includes a rupturable seal that maintains the liquid in the container isolated from ambient air until the seal is ruptured by insertion of the tubular member.

5. The oral irrigation device as defined in claim 4 wherein said male connecting module includes a generally cylindrical knob integral with the flange to enable insertion of the flange and rotation of the flange in relation to the female connecting module.

6. The oral irrigation device as defined in claim 5 wherein said housing includes a horizontal flange rotatably supporting said disk, said tabs being spaced from the disk a distance substantially equal to the thickness of the flange to enable the flange to underlie the tabs with the tabs holding the modules in sealed relation.

7. The oral irrigation device as defined in claim 6 wherein said container includes a storage compartment for the pump unit in the upper end thereof to provide a storage space for the pump unit when not in use.

8. The oral irrigation device as defined in claim 7 wherein said pump unit includes a top wall including a movable top wall portion forming a storage area for the discharge tube and nozzle on the pump unit.

9. The oral irrigation device as defined in claim 1 wherein said container includes a storage compartment for the pump unit in the upper end thereof to provide a storage space for the pump unit when not in use.

10. The oral irrigation device as defined in claim 9 wherein said storage compartment includes said container including a peripheral wall extending above the top wall to form a storage compartment and closure panels for the storage compartment.

11. An oral irrigation device comprising the combination of a packaged liquid and a pump unit, said packaged liquid including a container having a quantity of liquid therein formulated to treat surfaces within an oral cavity, said container including a top wall having a female connecting module therein, said pump unit including discharge nozzle means to discharge liquid onto surfaces of the oral cavity, an inlet tube communicated with the pump unit, said inlet tube including a male connecting module for separable, sealing connection with the female connecting module on the container to communicate the inlet tube with the interior of the container thereby enabling discharge of the liquid directly from the container onto the surfaces of the oral cavity without coming onto contact with ambient air, said pump unit including a top wall including a movable top wall portion forming a storage area for a discharge tube and nozzle on the pump unit.

* * * * *